(12) United States Patent
Saegusa et al.

(10) Patent No.: US 7,629,434 B2
(45) Date of Patent: Dec. 8, 2009

(54) FLUORINE-CONTAINING POLYMERIZABLE MONOMER AND POLYMER COMPOUND USING SAME

(75) Inventors: Hiroshi Saegusa, Shizuoka (JP); Satoru Narizuka, Saitama (JP); Kazuhiko Maeda, Tokyo (JP)

(73) Assignee: Central Glass Company, Limited, Ube-shi (JP)

( * ) Notice: Subject to any disclaimer, the term of this patent is extended or adjusted under 35 U.S.C. 154(b) by 520 days.

(21) Appl. No.: 10/586,184

(22) PCT Filed: Oct. 13, 2005

(86) PCT No.: PCT/JP2005/018839

§ 371 (c)(1),
(2), (4) Date: Jul. 14, 2006

(87) PCT Pub. No.: WO2006/041115

PCT Pub. Date: Apr. 20, 2006

(65) Prior Publication Data

US 2008/0234460 A1 Sep. 25, 2008

(30) Foreign Application Priority Data

Oct. 13, 2004 (JP) ............... 2004-299459
Sep. 28, 2005 (JP) ............... 2005-283105

(51) Int. Cl.
*C08G 63/06* (2006.01)
(52) U.S. Cl. .............. 528/361; 528/291; 560/19; 564/430
(58) Field of Classification Search ........ 528/361, 528/291; 560/19; 564/430
See application file for complete search history.

(56) References Cited

U.S. PATENT DOCUMENTS 3,594,418 A * 7/1971 Gilbert et al .............. 564/442
2008/0221298 A1* 9/2008 Yamanaka et al. ......... 528/291

FOREIGN PATENT DOCUMENTS

| JP | 1-246247 A | 10/1989 |
| JP | 1-261422 A | 10/1989 |
| JP | 2004-91329 A | 3/2004 |
| JP | 2006206879 | * 8/2006 |
| WO | WO 03/089404 A1 | 10/2003 |

OTHER PUBLICATIONS

"Latest Polyimide, its basic and application", edited by Japan Polyimide Study Group, pp. 426-429.

* cited by examiner

*Primary Examiner*—James Seidleck
*Assistant Examiner*—Gregory Listvoyb
(74) *Attorney, Agent, or Firm*—Crowell & Moring LLP

(57) ABSTRACT

Disclosed is a fluorine-containing polymerizable monomer represented by the formula [1] below. (In the formula, A represents a single bond, an oxygen atom, a sulfur atom, CO, $CH_2$, SO, $SO_2$, $C(CH_3)_2$, NHCO, $C(CF_3)_2$, a phenyl or an alicyclic ring; a and b independently represent an integer of 0-2; and $1 \leq a+b \leq 4$.) Such a fluorine-containing polymerizable monomer can be used as an effective polymerizable monomer exhibiting water repellency, oil repellency, low water absorbency, heat resistance, weather resistance, corrosion resistance, transparency, photosensitivity, low refractive index, low dielectric properties and the like. Consequently, the fluorine-containing polymerizable monomer can be applied to the field of advanced polymer materials.

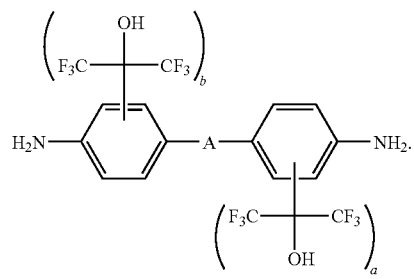

[1]

7 Claims, No Drawings

US 7,629,434 B2

FLUORINE-CONTAINING POLYMERIZABLE MONOMER AND POLYMER COMPOUND USING SAME

TECHNICAL FIELD

The present invention relates to a novel fluorine-containing polymerizable monomer and a novel polymer compound using the same.

BACKGROUND OF THE INVENTION

Polyamide and polyimide have been developed as representatives of organic polymers having high-degree heat resistance. They form a large market in electronic device field, engineering plastic field such as automotive and aerospace uses, fuel cell field, medical material field, optical material field, etc. At their center, many various polymers are put into practical use, such as polyimide represented by nylon, KEVLAR, etc.; polyamide acid and polyimide, which can be representative heat-resistant polymers; polyamide imide, which is a composite of them; and polybenzoxazole, polybenzthiazole, polybenzimidazole, etc. In particular, polyimide is again recently attracting attention as a material that is resistant to a lead-free solder step.

Polymerization of many of these heat-resistant polymers is conducted by successively generating a reaction, such as polyaddition or polycondensation, using plural types of monomers having a bifunctional or trifunctional reactive group in the molecule.

Regarding combinations of monomers in polymerization, there are known, in the case of polyamide, a method in which a diamine-type monomer is condensed with a dicarboxylic acid derivative, such as dicarboxylic acid, acid chloride or ester, and, in the case of polyamide acid or polyimide, a method by a polyaddition of diamine and acid dianhydride. As diamines that are generally used, aliphatic diamines, alicyclic diamines and aromatic diamines have been reported. From the viewpoint of polymerizability and heat resistance, however, there is preferably used an aniline-series monomer that has a supporting skeleton of a benzene single ring, biphenyl-type or polycyclic structure, in which a plurality of benzene rings are directly or indirectly bonded together, and that contains a plurality of amines in the molecule. On the other hand, in the case of polybenzoxazole and polybenzthiazole, there are used monomers having amine and hydroxyl group and amine and thiol group at ortho-positions of the benzene ring.

The purpose of simultaneously having an amine and another functional group in the molecule is explained, as follows. That is, there is conducted a design in which diamine is used as a polymerization site and at the same time hydroxyl group and thiol group are used as functional groups for intramolecular condensation cyclization, and in which a phenolic acid group is contained as a photosensitive functional group of these alkali-soluble groups and the like. However, there are reports of only the above-mentioned limited combinations in an attempt to contain plural types of functional groups together with diamine.

On the other hand, fluoro compounds have been developed or put into practical use in wide material fields, such as polyolefins and condensation polymers, mainly in advanced material fields, due to characteristics possessed by fluorine, such as water repellency, oil repellency, low water absorptive property, heat resistance, weather resistance, corrosion resistance, transparency, photosensitivity, low refractive index property and low dielectric property. In the condensation polymer field, an attempt to introduce fluorine into a diamine monomer has been conducted. There are reports of a diamine monomer in which hydrogen of the benzene ring has been replaced with fluorine atom or trifluoromethyl group, a diamine monomer in which a hexafluoroisopropenyl group has been introduced between two aromatic rings, and a fluorine-containing diamine monomer in which the benzene ring has been subjected to a hydrogen reduction. Furthermore, a bishydroxyamine monomer having a hexafluoroisopropenyl group as a central atomic group and aromatic hydroxyamines at its both sides has also been put into practical use. In this case, it is applied as a polybenzoxazole or hydroxyl-containing polyimide.

They are explained, for example, as fluorine-containing polybenzazoles in Non-patent Publication 1, etc. On the other hand, there have recently been conducted active researches and developments on photoresist materials, in which transparency of fluoro compounds in ultraviolet region, particularly in vacuum ultraviolet region, has been applied. It is an attempt to achieve adhesion to substrate, high glass transition point, photosensitivity due to acidity of fluorocarbinol group, alkali development property, etc., while achieving transparency at each wavelength for use by introducing fluorine. In particular, of fluorocarbinols, hexafluoroisopropyl group attracts attention due to its dissolution behavior, non-swelling property, high contrast, etc., and many researches and developments are conducted.

As assumed from photoresist development examples, hexafluoroisopropyl group, which is an acidic alcohol, has a potential for achieving a rapid, homogeneous, alkali solubility, while it maintains less swelling property. There have been, however, few reports of development examples of heat resistant polymers using a similar concept, that is, heat resistant polymers containing a hexafluoroisopropyl group as an acidic alcohol. Carboxylic group can be cited as a general acidic group. However, due to its high reactivity with amine, they say that it is difficult to make an amine having a carboxylic group in the same molecule exist stably.

Non-patent Publication 1: "Latest Polyimide, its basic and application" edited by Japan Polyimide Study Group, page 426.

SUMMARY OF THE INVENTION

It is an object of the present invention to find a novel, polymerizable monomer for polymer materials, which has surface characteristics (water repellency, oil repellency, etc.), resistances (heat resistance, weather resistance, corrosion resistance, etc.) and other characteristics (transparency, low refractive index property, low dielectric property, etc.) as fluorine-containing materials, together with alkali solubility, photosensitivity, organic solvent dissolution property, etc., and to provide a novel polymer compound that is obtained by using the same.

The present inventors have repeated an eager examination to solve the above-mentioned task. As a result, we have found a novel aniline compound, which has an atomic group, such as oxygen, at the center and aniline skeletons at its both ends, and in which at least one hydrogen atom on the anilines has been replaced with a hexafluoroisopropyl group, and a novel polymer compound using the same.

Furthermore, we have found that, in the case of a specific monomer having a hexafluoroisopropyl group at an ortho position of the amine, it involves a cyclization reaction, resulting in a novel polymer compound having many characteristics such as low dielectric property, heat resistance and solvent resistance, thereby completing the present invention.

According to the present invention, there is provided a fluorine-containing polymerizable monomer represented by the formula [1]

[Chem. 1]

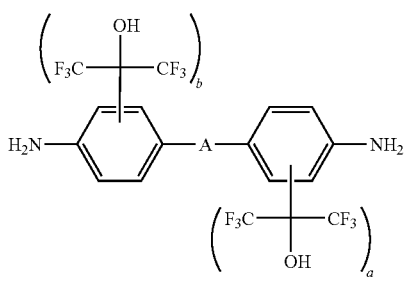

[1]

wherein A represents a single bond, oxygen atom, sulfur atom, CO, $CH_2$, SO, $SO_2$, $C(CH_3)_2$, NHCO, $C(CF_3)_2$, phenyl, or aliphatic ring; each of "a" and "b" independently represents an integer of 0-2; and $1 \leq a+b \leq 4$.

Furthermore, according to the present invention, there is provided a polymer compound derived from the fluorine-containing polymerizable monomer (dianiline).

DETAILED DESCRIPTION

As mentioned above, according to the present invention, it is possible to provide a novel, dianiline type, fluorine-containing, polymerizable monomer having a fluorocarbinol-type acidic group and a novel polymer compound using the same, by containing diamine and hexafluoroisopropyl group at the same time.

A fluorine-containing polymerizable monomer of the present invention has a plurality of polymerizable amines in the molecule and at the same time a hexafluoroisopropyl group(s). With this, it can be used as an effective polymerizable monomer, which can exhibit water repellency, oil repellency, low water absorptive property, heat resistance, weather resistance, corrosion resistance, transparency, photosensitivity, low refractive index property, low dielectric property, etc., and can be used for advanced polymer material fields. Furthermore, since hexafluoroisopropyl group is an acidic group having alkali solubility, it can also be used as a photosensitive insulating film for electronic devices, which has low dielectric property, high dissolution, high contrast, etc.

The above fluorine-containing polymerizable monomer represented by the formula [1] may be a fluorine-containing polymerizable monomer represented by the following formula [2] or formula [3] (in the formulas [2] and [3], the definition of A is the same as that of the formula [1]).

[Chem. 2]

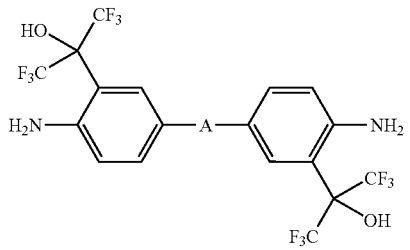

[2]

[Chem. 3]

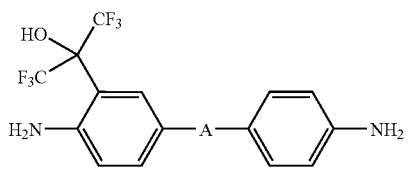

[3]

As the polymerizable monomer of the formula [1] usable in the present invention is specifically exemplified, the following formula [4], formula [5], formula [11a], formula [11b], formula [11c] and formulas [12] to [24] are cited, but it is not limited to these.

[Chem. 4]

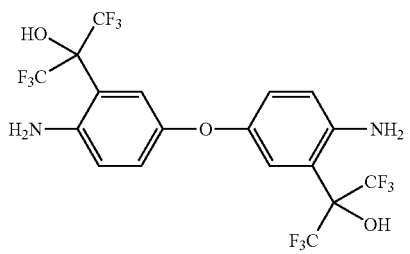

[4]

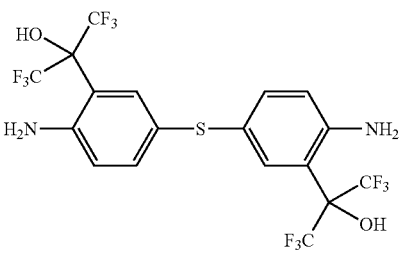

[11a]

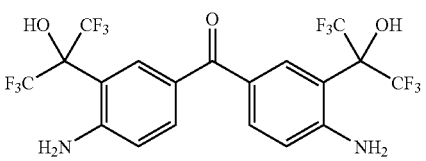

[11b]

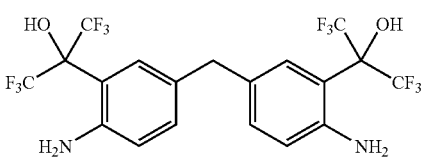

[11c]

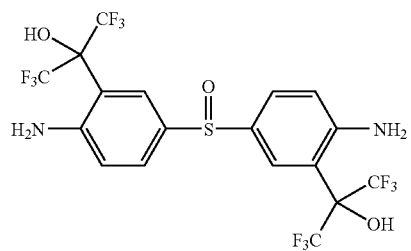
[12]
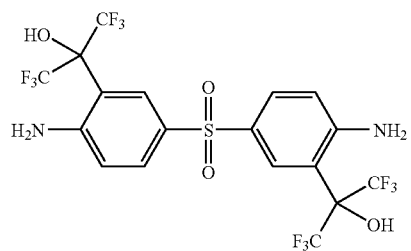
[13]
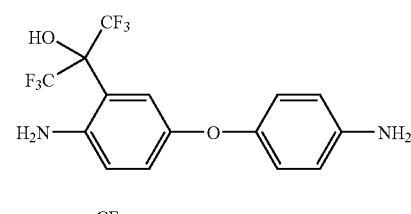
[5]
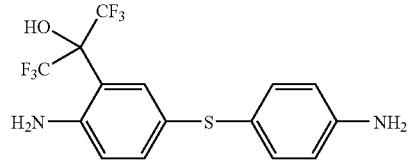
[14]
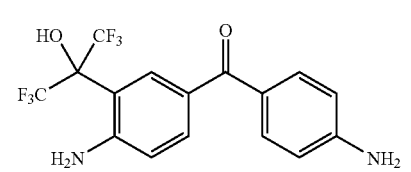
[15]
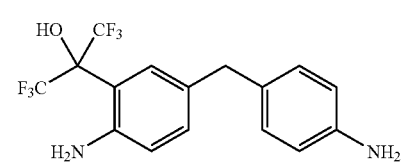
[16]
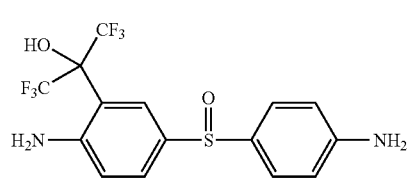
[17]
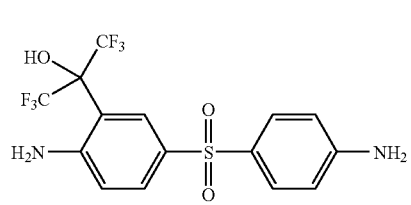
[18]
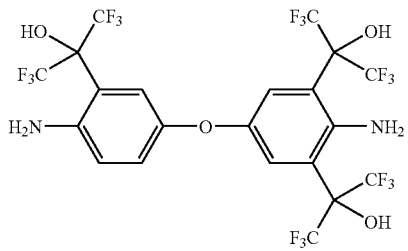
[19]
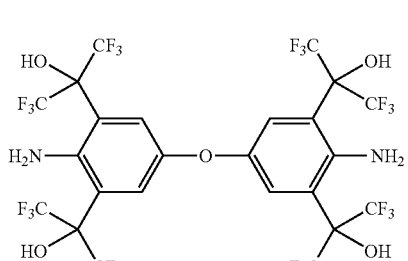
[20]
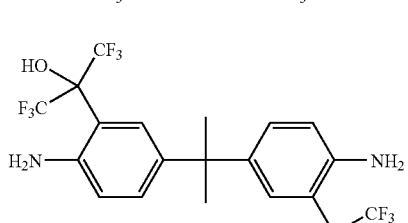
[21]
[22]
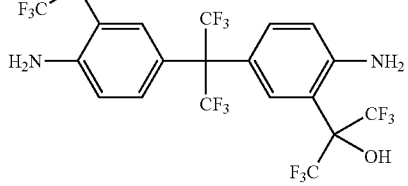
[23]
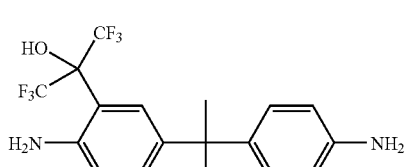
[24]
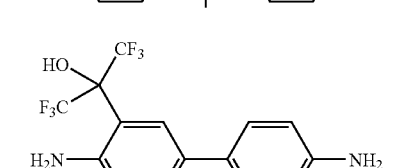
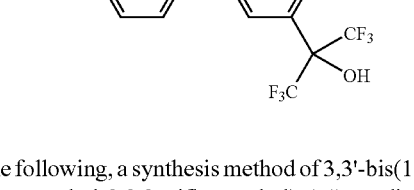
In the following, a synthesis method of 3,3'-bis(1-hydroxy-1-trifluoromethyl-2,2,2-trifluoroethyl)-4,4'-oxydianiline, which is a monomer represented by the formula [4],

[Chem. 5]

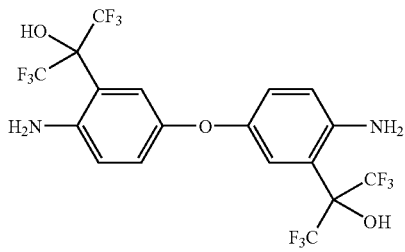

[4]

as a representative example of the formula [1] is explained.

This monomer is obtained by reacting 4,4'-oxydianiline with hexafluoroacetone or hexafluoroacetone trihydrate.

In the case of using hexafluoroacetone, the reaction is conducted by introducing hexafluoroacetone into 4,4'-oxydianiline as a raw material. Since boiling point of hexafluoroacetone is low (−28° C.), it is preferable to use an apparatus (a cooling apparatus or sealed reactor) for preventing outflow of hexafluoroacetone toward the outside of the reaction system. A sealed reactor is particularly preferable as the apparatus.

In the case of using hexafluoroacetone trihydrate, the reaction can be started by mixing together 4,4'-oxydianiline as a raw material and hexafluoroacetone trihydrate at the same time. Since boiling point of hexafluoroacetone trihydrate is relatively high (105° C.), its handling is easy as compared with hexafluoroacetone (boiling point: −28° C.). In this case, a sealed container can also be used. It is, however, possible to sufficiently prevent outflow of hexafluoroacetone trihydrate toward the outside of the reaction system, even by allowing tap water (room temperature) to flow through a normal reflux condenser.

Hexafluoroacetone has a reactivity higher than that of hexafluoroacetone trihydrate. Depending on the reaction condition, hexafluoroacetone reacts with an amino group on the aniline skeleton. With this, it is likely to generate by-products (imines) represented by the following formulas [25] to [28].

[Chem. 6]

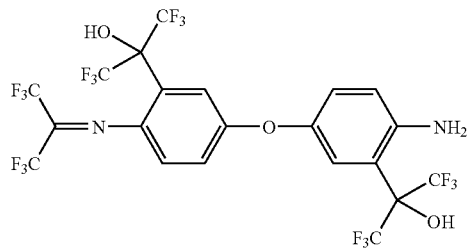

[25]

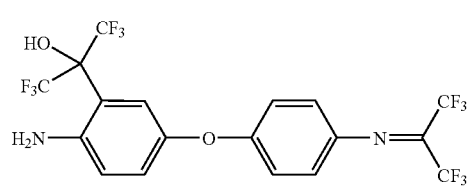

[26]

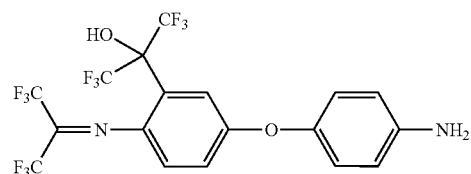

[27]

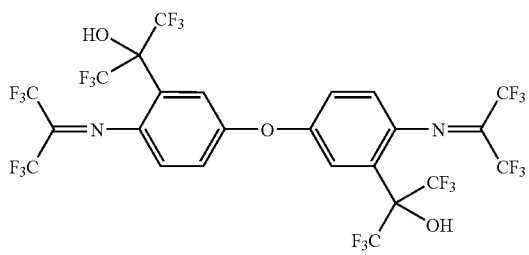

[28]

As mentioned hereinabove, it is particularly preferable to use hexafluoroacetone trihydrate in the production of 3,3'-bis (1-hydroxy-1-trifluoromethyl-2,2,2-trifluoroethyl)-4,4'-oxydianiline from the viewpoints of handling easiness, apparatus simplicity and high product selectivity.

The amount of hexafluoroacetone or hexafluoroacetone trihydrate is preferably 2 equivalents to 10 equivalents, more preferably 2.5 equivalents to 5 equivalents, relative to 4,4'-oxydianiline. The reaction proceeds without problem even by using more than this, but it is not preferable from economical viewpoint.

The present reaction is conducted normally in a temperature range of room temperature to 180° C., preferably 50° C. to 150° C., particularly preferably 90° C. to 130° C. A case, in which it is lower than room temperature, is not preferable, since the reaction hardly proceeds. A temperature exceeding 180° C. is not preferable, since side reactions proceed.

Although the present reaction can be conducted without using catalyst, it is possible to accelerate the reaction by using an acid catalyst. As the catalyst used, aluminum chloride, iron (III) chloride, Lewis acids such as boron fluoride, and organic sulfonic acids such as benzenesulfonic acid, camphorsulfonic acid (CSA), methanesulfonic acid, p-toluenesulfonic acid (pTsOH), paratoluenesulfonic acid (pTsOH) monohydrate and pyridiniumparatoluene sulfonate (PPTS) are preferable. Of these, aluminum chloride, iron (III) chloride, methanesulfonic acid and p-toluenesulfonic acid (pTsOH) monohydrate are particularly preferable. The amount of the catalyst used is preferably 1 mol % to 50 mol %, particularly preferably 3 mol % to 40 mol %, relative to one mole of 4,4'-oxydianiline. The reaction proceeds without problem even by using more than this, but it is not preferable from economical viewpoint.

Although the present reaction can be conducted without using solvent, it is also possible to use solvent. The solvent to be used is not particularly limited as long as it is not involved in the reaction. An aromatic hydrocarbon, such as xylene, toluene, benzene, anisole, diphenyl ether, nitrobenzene and benzonitrile, or water is preferable. The amount of the solvent to be used is not particularly limited, but the use in a large amount is not preferable since yield per volume lowers.

In the case of conducting the present reaction in a sealed reactor (autoclave), the mode is different depending on the use of hexafluoroacetone or hexafluoroacetone trihydrate. In the case of using hexafluoroacetone, the reactor is charged firstly with 4,4'-oxydianiline and according to need catalyst and/or solvent. Then, it is preferable to successively introduce hexafluoroacetone, while increasing the temperature in a manner that the reactor inside pressure does not exceed 0.5 MPa.

In the case of using hexafluoroacetone trihydrate, it is possible to firstly introduce 4,4'-oxydianiline and a necessary amount of hexafluoroacetone trihydrate. Furthermore, according to need, it is possible to conduct the reaction by introducing catalyst and/or solvent into the reactor.

Although the reaction time of the present reaction is not particularly limited, the optimum reaction time is different depending on the temperature, the amount of catalyst used, etc. Therefore, it is preferable to terminate the present step, after confirming that the raw material has sufficiently been consumed by conducting the reaction, while measuring the progress condition of the reaction by a general-purpose analysis means such as gas chromatography. After the termination of the reaction, it is possible to obtain 3,3'-bis(1-hydroxy-1-trifluoromethyl-2,2,2-trifluoroethyl)-4,4'-oxydianiline by normal means such as extraction, distillation and crystallization. According to need, it is also possible to conduct a purification by column chromatography or recrystallization, etc.

In the following, a synthesis method of 3-(1-hydroxy-1-trifluoromethyl-2,2,2-trifluoroethyl)-4,4'-oxydianiline, which is a monomer represented by the formula [5],

[Chem. 7]

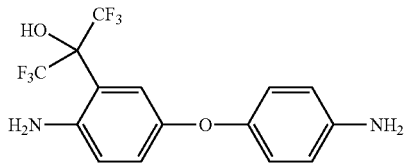

[5]

as a representative example of the formula [1] is explained.

The synthesis of this monomer can be conducted in accordance with the above-mentioned synthesis method of 3,3'-bis (1-hydroxy-1-trifluoromethyl-2,2,2-trifluoroethyl)-4,4'-oxydianiline, except in that the amount of hexafluoroacetone or hexafluoroacetone trihydrate to be used is reduced.

Specifically, the amount of hexafluoroacetone or hexafluoroacetone trihydrate used upon the synthesis of the present monomer is preferably 1 equivalent to 5 equivalents, more preferably 1.5 equivalents to 3 equivalents, relative to 4,4'-oxydianiline. The reaction proceeds without problem even by using more than this, but it is not preferable from economical viewpoint.

It is possible to control the number of hexafluoroisopropyl groups to be introduced onto the 4,4'-oxydianiline skeleton by controlling the amount of hexafluoroacetone or hexafluoroacetone trihydrate used.

The production of other fluorine-containing polymerizable monomers represented by the formula [1] can also be conducted in accordance with the above-mentioned synthesis method of 3,3'-bis(1-hydroxy-1-trifluoromethyl-2,2,2-trifluoroethyl)-4,4'-oxydianiline.

Next, an exemplary method for using a fluorine-containing polymerizable monomer according to the present invention is explained. The fluorine-containing polymerizable monomer of the present invention is a dianiline and is a compound having at least one hexafluoroisopropyl group, and has at least three functional groups at the same time in the molecule. In the case of producing a polymer, these at least three functional groups are effectively used. Specifically, it is preferable to use dianiline.

It is possible to use a dicarboxylic acid monomer as a partner of the dianiline, which is the fluorine-containing polymerizable monomer of the present invention, thereby synthesizing a polyamide resin as a polymer produced. In this case, it is possible to use dicarboxylic acid monomer and its derivatives such as dicarboxylic acid dihalides (halogen is chlorine, bromine, fluorine, or iodine), dicarboxylic acid monoesters, and dicarboxylic acid diesters.

As a polymerizable monomer that becomes a partner of the fluorine-containing polymerizable monomer of the present invention is exemplified, there are cited dicarboxylic acids and their ester derivatives, which are represented by the formula [29] and dicarboxylic acid halides, which are represented by the formula [30].

[Chem. 8]

[29]

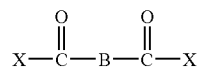

[30]

Herein, each R is independently a hydrogen; an alkyl group such as methyl, ethyl, propyl, isopropyl or butyl group; a benzyl group, or the like. B is a bivalent organic group containing at least one selected from aliphatic rings, aromatic rings and alkylene groups, it may contain fluorine, chlorine, oxygen, sulfur or nitrogen, and its hydrogens may be partially replaced with alkyl group, fluoroalkyl group, carboxylic group, hydroxyl group or cyano group. X represents a halogen atom (chlorine, fluorine, bromine or iodine).

As the dicarboxylic acid usable in the present invention is exemplified in the form of dicarboxylic acid, it can be exemplified by aliphatic dicarboxylic acids such as oxalic acid, malonic acid, succinic acid, glutaric acid, adipic acid, pimelic acid, suberic acid, azelaic acid, and sebacic acid; and aromatic dicarboxylic acids such as phthalic acid, isophthalic acid, terephthalic acid, 3,3'-dicarboxyldiphenyl ether, 3,4'-dicarboxyldiphenyl ether, 4,4'-dicarboxyldiphenyl ether, 3,3'-dicarboxyldiphenylmethane, 3,4'-dicarboxyldiphenylmethane, 4,4'-dicarboxyldiphenylmethane, 3,3'-dicarboxyldiphenyldifluoromethane, 3,3'-dicarboxyldiphenyldifluoromethane, 3,4'-dicarboxyldiphenyldifluoromethane, 4,4'-dicarboxyldiphenyldifluoromethane, 3,3'-dicarboxyldiphenyl sulfone, 3,4'-dicarboxyldiphenyl sulfone, 4,4'-dicarboxyldiphenyl sulfone, 3,3'-dicarboxyldiphenyl sulfide, 3,4-dicarboxyldiphenyl sulfide, 4,4'-dicarboxyldiphenyl sulfide, 3,3'-dicarboxyldiphenyl ketone, 3,4'-dicarboxyldiphenyl ketone, 4,4'-dicarboxyldiphenyl ketone, 2,2-bis(3-carboxyphenyl)propane, 2,2-bis(3,4'-dicarboxyphenyl)propane, 2,2-bis(4-carboxyphenyl)propane, 2,2-bis (3-carboxyphenyl)hexafluoropropane, 2,2-bis(3,4'-dicarboxyphenyl)hexafluoropropane, 2,2-bis(4-carboxyphenyl) hexafluoropropane, 1,3-bis(3-carboxyphenoxy)benzene, 1,4-bis(3-carboxyphenoxy)benzene, 1,4-bis(4-carboxyphenoxy)benzene, 3,3'-(1,4-phenylenebis(1-methylethylidene)) bisbenzoic acid, 3,4'-(1,4-phenylenebis(1-methylethylidene))bisbenzoic acid, 4,4'-(1,4-phenylenebis(1-methylethylidene))bisbenzoic acid, 2,2-bis(4-(3- carboxyphenoxy)phenyl)propane, 2,2-bis(4-(4-carboxyphenoxy)phenyl)propane, 2,2-bis(4-(3-carboxyphenoxy)phenyl)hexafluoropropane, 2,2-bis(4-(4-carboxyphenoxy)phenyl)hexafluoropropane, bis(4-(3-carboxyphenoxy)phenyl)sulfide, bis(4-(4-carboxyphenoxy)phenyl)sulfide, bis(4-(3-carboxyphenoxy)phenyl)sulfone, bis(4-(4-carboxyphenoxy)phenyl)sulfone; perfluorononenyloxy group-containing dicarboxylic acids such as 5-(perfluorononenyloxy)isophthalic acid, 4-(perfluorononenyloxy)phthalic acid, 2-(perfluorononenyloxy)terephthalic acid, and 4-methoxy-5-(perfluorononenyloxy)isophthalic acid; and perfluorohexenyloxy group-containing dicarboxylic acids such as 5-(perfluorohexenyloxy)isophthalic acid, 4-(perfluorohexenyloxy)phthalic acid, 2-(perfluorohexenyloxy)terephthalic acid, and 4-methoxy-5-(perfluorohexenyloxy)isophthalic acid.

By conducting a polymerization using a monomer represented by any of the formulas [1] to [5], there is obtained a polymer compound represented by the formula [6],

[Chem. 9]

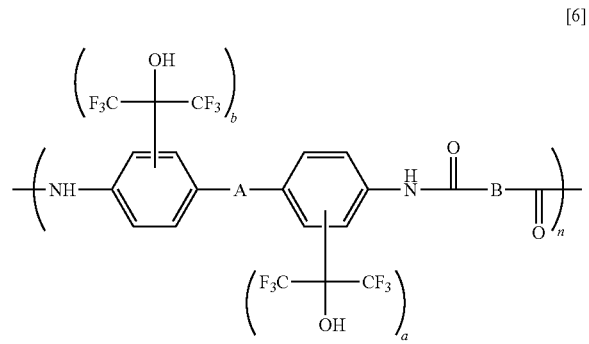

[6]

wherein "A", "a" and "b" are defines as in the formula [1]. B is a bivalent organic group containing at least one selected from aliphatic rings, aromatic rings and alkylene groups, it may contain fluorine, chlorine, oxygen, sulfur or nitrogen, and its hydrogens may be partially replaced with alkyl group, fluoroalkyl group, carboxylic group, hydroxyl group or cyano group. "n" represents polymerization degree.

As one example of the polymerization reaction, for example, if a fluorine-containing polymerizable monomer represented by the formula [1] of the present invention is reacted with the above dicarboxylic acid monomer (formula [29] or formula [30]), a polymer compound (polyamide resin) represented by the formula [6] is obtained.

This polymerization reaction is not particularly limited in terms of method and condition. For example, it is possible to cite a method in which the above diamine component and an amide-forming derivative of the above dicarboxylic acid are mutually dissolved (melted) at 150° C. or higher to have a reaction without solvent, a method in which the reaction is conducted at high temperature (preferably 150° C. or higher) in an organic solvent, and a method in which the reaction is conducted at a temperature of −20 to 80° C. in an organic solvent.

Usable organic solvent is not particularly limited, as long as both components of the raw materials are dissolved therein. It can be exemplified by amide solvents such as N,N-dimethylformamide, N,N-dimethylacetamide, N-methylformamide, hexamethylphosphoric acid triamide, and N-methyl-2-pyrrolidone; aromatic solvents such as benzene, anisole, diphenyl ether, nitrobenzene, and benzonitrile; halogen-series solvents such as chloroform, dichloromethane, 1,2-dichloroethane, and 1,1,2,2-tetrachloroethane; and lactones such as γ-butyrolactone, γ-valerolactone, δ-valerolactone, γ-caprolactone, ε-caprolactone, α-methyl-γ-butyrolactone. It is effective to conduct the reaction with such organic solvent under coexistence with an acid acceptor such as pyridine and triethylamine. In particular, if the above amide solvents are used, these solvents themselves become acid acceptors. Therefore, it is possible to obtain polyamide resins of high degree of polymerization.

A fluorine-containing polymerizable monomer of the present invention can turn into copolymers by combinations with other diamines and dihydroxyamine, etc. The combinable diamine compound can be exemplified by 3,5-diaminobenzotrifluoride, 2,5-diaminobenzotrifluoride, 3,3'-bistrifluoromethyl-4,4'-diaminobiphenyl, 3,3'-bistrifluoromethyl-5,5'-diaminobiphenyl, bis(trifluoromethyl)-4,4'-diaminodiphenyl, bis(fluorinated alkyl)-4,4'-diaminodiphenyl, dichloro-4,4'-diaminodiphenyl, dibromo-4,4'-diaminodiphenyl, bis(fluorinated alkoxy)-4,4'-diaminodiphenyl, diphenyl-4,4'-diaminodiphenyl, 4,4'-bis(4-aminotetrafluorophenoxy)tetrafluorobenzene, 4,4'-bis(4-aminotetrafluorophenoxy)octafluorobiphenyl, 4,4'-binaphthylamine, o-, m- and p-phenylenediamines, 2,4-diaminotoluene, 2,5-diaminotoluene, 2,4-diaminoxylene, 2,4-diaminodurene, dimethyl-4,4'-diaminodiphenyl, dialkyl-4,4'-diaminodiphenyl, dimethoxy-4,4'-diaminodiphenyl, diethoxy-4,4'-diaminodiphenyl, 4,4'-diaminodiphenylmethane, 4,4'-diaminodiphenyl ether, 3,4'-diaminodiphenyl ether, 4,4'-diaminodiphenylsulfone, 3,3'-diaminodiphenylsulfone, 4,4'-diaminobenzophenone, 3,3'-diaminobenzophenone, 1,3-bis(3-aminophenoxy)benzene, 1,3-bis(4-aminophenoxy)benzene, 1,4-bis(4-aminophenoxy)benzene, 4,4'-bis(4-aminophenoxy)biphenyl, bis(4-(3-aminophenoxy)phenyl)sulfone, bis(4-(4-aminophenoxy)phenyl)sulfone, 2,2-bis(4-(4-aminophenoxy)phenyl)propane, 2,2-bis(4-(4-aminophenoxy)phenyl)hexafluoropropane, 2,2-bis(4-(3-aminophenoxy)phenyl)propane, 2,2-bis(4-(3-aminophenoxy)phenyl)hexafluoropropane, 2,2-bis(4-(4-amino-2-trifluoromethylphenoxy)phenyl)hexafluoropropane, 2,2-bis(4-(3-amino-5-trifluoromethylphenoxy)phenyl)hexafluoropropane, 2,2-bis(4-aminophenyl)hexafluoropropane, 2,2-bis(3-aminophenyl)hexafluoropropane, 2,2-bis(3-amino-4-hydroxyphenyl)hexafluoropropane, 2,2-bis(3-amino-4-methylphenyl)hexafluoropropane, 4,4'-bis(4-aminophenoxy)octafluorobiphenyl, 4,4'-diaminobenzanilide, etc. At least two of these can be combined.

Regarding a fluorine-containing polymerizable monomer of the present invention, it is also possible to protect the hexafluoropropyl group and introduce a protecting group (acid-labile group) that is released by acid. Acid-labile groups can be used without limitation, as long as they are groups that generate release by the effect of photoacid generator, hydrolysis, etc. As specific examples, it is possible to cite alkoxycarbonyl groups such as tert-butoxycarbonyl group, tert-amyloxycarbonyl group, methoxycarbonyl group, and ethoxycarbonyl group; acetal groups such as methoxymethyl group, ethoxyethyl group, butoxyethyl group, cyclohexyloxyethyl group, and benzyloxyethyl group; silyl groups such as trimethylsilyl group, ethyldimethylsilyl group, methyldiethylsilyl group, and triethylsilyl group; acyl groups such as acetyl group, propionyl group, butyryl group, heptanoyl group, hexanoyl group, valeryl group, and pivaloyl group.

By introducing an acid-releasing group, a polymer compound obtained by polymerization using a fluorine-containing polymerizing monomer of the present invention can be used as a resist material. That is, the hexafluoroisopropanol group in the molecule is protected with an acid-labile protecting group. Then, it is mixed with a photoacid generator to produce a resist. By exposing this, the acid labile group is released, thereby forming a hexafluoroisopropanol group. As a result, an alkali development becomes possible. Thus, it is useful as a positive-type resist or photosensitive material.

A fluorine-containing polymerizing monomer of the present invention can be used with other functional groups. For example, it is possible to introduce a crosslinking site by providing an unsaturated bond. For example, if a fluorine-containing polymerizing monomer of the present invention is reacted with maleic anhydride, it turns into a bismaleimide. With this, it is possible to introduce a double bond. This compound is useful as a crosslinking agent.

It is possible to obtain a polymer compound represented by the formula [7] or the formula [8],

[Chem. 10]

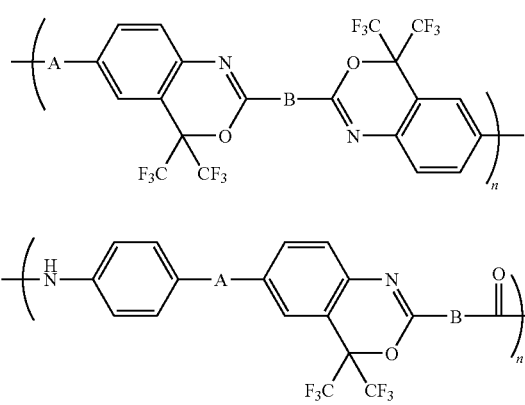

(in the formula, A, B and n are defined as in the general formula [6]) by subjecting a polymer compound represented by the formula [6] of the present invention to cyclization (cyclization condensation). A polymer compound represented by the formula [6] can be obtained, for example, by a polymerization using a monomer represented by the formula [2] or [3].

The cyclization reaction is not particularly limited. The cyclization can be conducted by various methods that accelerate the dehydration condition, such as heat and acid catalyst.

In the case of cyclization, it is possible to conduct a resin modification accompanied with significant changes in terms of physical properties, such as heat resistance improvement, dissolution change, lowering in refractive index and dielectric constant, and achievement of water repellency and oil repellency. In particular, a fluorine-containing polymer compound represented by the formula [7] or [8] of the present invention is further improved in heat resistance, since it has a cyclic structure in the molecule.

As a partner of the dianiline, which is a fluorine-containing polymerizable monomer of the present invention, it is possible to use a tetracarboxylic acid derivative, for example, a tetracarboxylic acid dianhydride represented by the formula [31]

[Chem. 11]

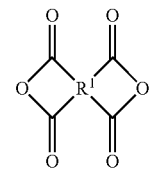

wherein $R^1$ is a tetravalent organic group containing at least one selected from aliphatic rings, aromatic rings and alkylene groups, it may contain fluorine, chlorine, oxygen, sulfur or nitrogen, and its hydrogens may be partially replaced with alkyl group, fluoroalkyl group, carboxylic group, hydroxyl group or cyano group. The tetracarboxylic acid dianhydride of this case can be used without particular limitation, as long as it has a structure generally used as a polyamide acid or polyimide raw material.

Such tetracarboxylic acid dianhydride is not particularly limited in structure. For example, it is possible to cite benzenetetracarboxylic acid dianhydride (pyromellitic acid dianhydride; PMDA), trifluoromethylbenzenetetracarboxylic acid dianhydride, bistrifluoromethylbenzenetetracarboxylic acid dianhydride, difluorobenzenetetracarboxylic acid dianhydride, naphthalenetetracarboxylic acid dianhydride, biphenyltetracarboxylic acid dianhydride, terphenyltetracarboxylic acid dianhydride, hexafluoroisopropylidenediphthalic acid dianhydride, oxydiphthalic acid dianhydride, bicyclo(2,2,2)oct-7-ene-2,3,5,6-tetracarboxylic acid dianhydride, 2,2-bis(3,4-dicarboxyphenyl)hexafluoropropanoic acid dianhydride (6FDA), 2,3,4,5-thiophenetetracarboxylic acid dianhydride, 2,5,6,2≡,5≡,6≡-hexafluoro-3,3',4,4'-biphenyltetracarboxylic acid dianhydride, bis(3,4-dicarboxyphenyl)sulfonic acid dianhydride, 3,4,9,10-perylenetetracarboxylic acid dianhydride, etc. In particular, pyromellitic acid and 6FDA are preferable. These tetracarboxylic acid dianhydrides may be used alone or in a mixture of at least two. In the present invention, in connection with the ratio in use of the tetracarboxylic acid dianhydride and the amine component, it is used in 0.9-1.1 moles, preferably 0.95-1.05 moles, more preferably 0.98-1.03 moles, relative to 1 mole of the tetracarboxylic acid dianhydride. If it is outside of this range, the molar ratio balance is lost, and its properties are impaired. Therefore, it is not preferable.

According to the present invention, as a novel polymer compound that is synthesized by using a monomer represented by the formula [1], there is provided a polymer compound represented by the formula [9],

[Chem. 12]

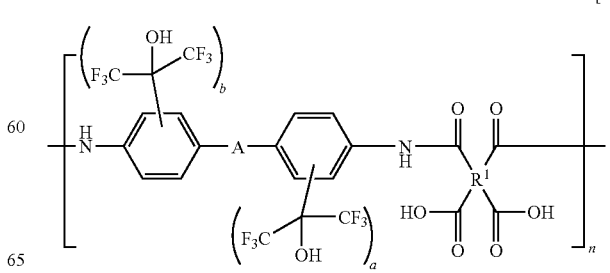

wherein "A", "a" and "b" are the same as those of the formula [1], R¹ is a tetravalent organic group containing at least one selected from aliphatic rings, aromatic rings and alkylene groups, it may contain fluorine, chlorine, oxygen, sulfur or nitrogen, and its hydrogens may be partially replaced with alkyl group, fluoroalkyl group, carboxylic group, hydroxyl group or cyano group. "n" represents degree of polymerization.

As one example of the polymerization reaction, a polymer compound (polyamide acid) represented by the formula [9] is obtained, for example, by reacting a fluorine-containing polymerizable monomer represented by the formula [1] of the present invention with the above tetracarboxylic acid dianhydride.

Regarding method and condition of the polymerization reaction, it is possible to use a polymerization method and a polymerization condition, which are similar to those of the reactions with dicarboxylic acids. The usable solvent is not particularly limited, as long as both components of the raw materials are dissolved therein. It is possible to use a solvent that is similar to those in the reactions with the dicarboxylic acids. It can be exemplified by amide solvents such as N,N-dimethylformamide, N,N-dimethylacetamide, N-methylformamide, hexamethylphosphoric triamide, and N-methyl-2-pyrolidone; aromatic solvents such as benzene, anisole, diphenyl ether, nitrobenzene, and benzonitrile; halogen-series solvents such as chloroform, dichloromethane, 1,2-dichloroethane, and 1,1,2,2-tetrachloroethane; lactones such as γ-butyrolactone, γ-valerolactone, δ-valerolactone, γ-caprolactone, ε-caprolactone, and α-methyl-γ-butyrolactone. It is effective to conduct the reaction with such organic solvent under coexistence with an acid acceptor such as pyridine and triethylamine.

Similar to the reactions with dicarboxylic acids, it can also be turned into a copolymer by a combination with other diamines and dihydroxyamines. As a combinable diamine compound, it is possible to use the above diamine. Similar to the above, it can also be a combination of at least two.

According to the present invention, as a novel polymer compound that is obtained by subjecting a polymer compound represented by the formula [9] to a cyclization condensation, there is provided a polymer compound represented by the formula [10],

[Chem. 13]

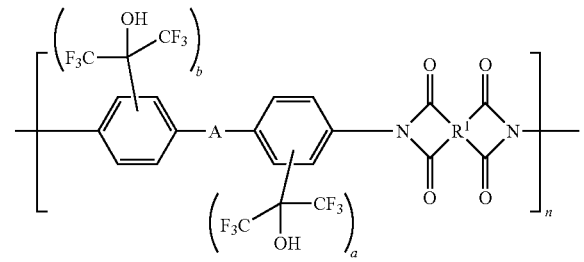

[10]

wherein "A", "a" and "b" are the same as those of the formula [1], R¹ is a tetravalent organic group containing at least one selected from aliphatic rings, aromatic rings and alkylene groups, it may contain fluorine, chlorine, oxygen, sulfur or nitrogen, and its hydrogens may be partially replaced with alkyl group, fluoroalkyl group, carboxylic group, hydroxyl group or cyano group. "n" represents degree of polymerization.

The above polyamide acid represented by the formula [9] can be turned into a fluorine-containing alicyclic polyimide represented by the formula [10] through an imidization reaction by heating or dehydration agent. In the case of conducting the heating imidization, the treatment is possible at a temperature of 80-400° C. In particular, a temperature range of 150-350° C. is preferable. In case that the imidization temperature is lower than 150° C., the degree of imidization is low, and thereby the film strength of the polyimide film is impaired. Therefore, it is not preferable. In case that it is higher than 350° C., the coating film becomes colored or brittle. Therefore, it is problematic. It can be chemically conducted by the reaction with a dehydration agent, such as acetic anhydride, in place of the heating treatment.

The fluorine-containing polymer of the present invention can be used in the condition of a varnish dissolved in an organic solvent or in the powder condition, film condition, or solid condition. Upon this, according to need, the obtained polymer may be mixed with an additive such as oxidation stabilizer, filler, silane coupling agent, photosensitive agent, photopolymerization initiator and sensitizer. In the case of using it as a varnish, it can be applied to a substrate, such as glass, silicon wafer, metal, metal oxide, ceramic, and resin, by a method normally used, such as spin coating, spraying, flow coating, impregnation coating, and brush coating.

Furthermore, n (degree of polymerization) in the general formulas [6] to [10] refers to the number (a positive integer) of the repeating units depending on the degree of polymerization and is preferably 5-10000, more preferably 10-1000. The polymer of the present invention is a mixture of polymers having a certain width of polymerization degree. The polymer weight average molecular weight is generally preferably 1000 to 5000000, particularly preferably 2000 to 200000. The polymerization degree and the molecular weight can be set to desired values by suitably adjusting the after-mentioned polymerization method conditions.

EXAMPLES

In the following, the present invention is described in more detail by examples. The present invention is, however, not limited to the examples.

Example 1

Production of 3,3'-bis(1-hydroxy-1-trifluoromethyl-2,2,2-trifluoroethyl)-4,4'-oxydianiline (formula [4])

A 100 ml, glass, sealed container (autoclave) was charged with 5.00 g (25.0 mmol) of 4,4'-oxydianiline, 237 mg (1.25 mmol, 5 mol %) of p-toluenesulfonic acid monohydrate, and 15 ml of xylene, and the inside of the system was turned into a nitrogen atmosphere. Then, the temperature increase was started. After the inside temperature of the reaction liquid was set to 120° C., 12.4 g (74.9 mmol, 3 equivalents) of hexafluoroacetone were introduced. After the reaction was conducted at an inside temperature of 120° C. for 23 hours, the reaction liquid was cooled down.

The reaction liquid was found by gas chromatography (GC) analysis to contain 39.8% of the target compound, 3,3'-bis(1-hydroxy-1-trifluoromethyl-2,2,2-trifluoroethyl)-4,4'-oxydianiline, 5.4% of 3-(1-hydroxy-1-trifluoromethyl-2,2,2-trifluoroethyl)-4,4'-oxydianiline, and 53.0% of the total of various imines produced by the reaction of hexafluoroacetone with the amine moiety of 4,4'-oxydianiline. After adding 50 ml of water to the reaction liquid, stirring was conducted. This mixed liquid was filtered, followed by washing with water and then vacuum drying, thereby obtaining 4.30 g of the target compound, 3,3'-bis(1-hydroxy-1-trifluoromethyl-2,2, 2-trifluoroethyl)-4,4'-oxydianiline (yield: 33%; purity: 80.7%).

Example 2

Production of 3,3'-bis(1-hydroxy-1-trifluoromethyl-2,2,2-trifluoroethyl)-4,4'-oxydianiline (formula [4])

A 200 ml, four-necked, round-bottom flask was charged with 25.0 g (125 mmol) of 4,4'-oxydianiline, 4.75 g (25.0 mmol, 20 mol %) of p-toluenesulfonic acid monohydrate, and 82.5 g (375 mmol, 3 equivalents) of hexafluoroacetone trihydrate, and the inside of the system was turned into a nitrogen atmosphere. Then, the temperature increase was started, and the inside temperature of the reaction liquid was set to 105° C. After stirrings for 23 hours and 46 hours, 2.37 g (12.5 mmol, 10 mol %) of p-toluenesulfonic acid monohydrate and 27.5 g (125 mmol, 1 equivalent) of hexafluoroacetone trihydrate were respectively added. After stirring for 53 hours in total, the reaction liquid was cooled down.

The reaction liquid was found by gas chromatography (GC) analysis to contain 60.1% of the target compound, 3,3'-bis(1-hydroxy-1-trifluoromethyl-2,2,2-trifluoroethyl)-4,4'-oxydianiline, 25.0% of 3-(1-hydroxy-1-trifluoromethyl-2,2,2-trifluoroethyl)-4,4'-oxydianiline, and 14.4% of the total of various imines produced by the reaction of hexafluoroacetone with the amine moiety of 4,4'-oxydianiline. 100 ml of water were added to the reaction liquid, followed by extraction with 100 ml of ethyl acetate. Then, the organic layer was washed with 50 ml of saturated sodium hydrogencarbonate aqueous solution. The organic layer was dried with magnesium sulfate, followed by filtration and distilling the solvent off, thereby obtaining 112 g of crude 3,3'-bis(1-hydroxy-1-trifluoromethyl-2,2,2-trifluoroethyl)-4,4'-oxydianiline (purity: 50.7%). This crude product was recrystallized in toluene, thereby obtaining 41.0 g of the target 3,3'-bis(1-hydroxy-1-trifluoromethyl-2,2,2-trifluoroethyl)-4,4'-oxydianiline (yield: 62%; purity: 95.7%).

Example 3

Production of 3,3'-bis(1-hydroxy-1-trifluoromethyl-2,2,2-trifluoroethyl)-4,4'-oxydianiline (Formula [4])

A 100 ml, glass, sealed container (autoclave) was charged with 6.30 g (31.5 mmol) of 4,4'-oxydianiline, 598 mg (3.15 mmol, 10 mol %) of p-toluenesulfonic acid monohydrate, and 27.7 g (126 mmol, 3 equivalents) of hexafluoroacetone trihydrate, and the inside of the system was turned into a nitrogen atmosphere. Then, the temperature increase was started, and the inside temperature of the reaction liquid was set to 120° C. After stirring for 22 hours, the reaction liquid was cooled down.

The reaction liquid was found by gas chromatography (GC) analysis to contain 59.0% of the target compound, 3, 3'-bis(1-hydroxy-1-trifluoromethyl-2,2,2-trifluoroethyl)-4, 4'-oxydianiline, 9.3% of 3-(1-hydroxy-1-trifluoromethyl-2,2,2-trifluoroethyl)-4,4'-oxydianiline, and 28.8% of the total of various imines produced by the reaction of hexafluoroacetone with the amine moiety of 4,4'-oxydianiline. 50 ml of toluene were added to the reaction liquid, followed by heating dissolution. After cooling, the precipitated solid matter was filtered, followed by vacuum drying. 15.2 g of crude 3,3'-bis(1-hydroxy-1-trifluoromethyl-2,2,2-trifluoroethyl)-4,4'-oxydianiline (yield: 91%; purity: 88.2%) were obtained. This crude product was recrystallized in toluene, thereby obtaining 12.0 g of the target 3,3'-bis(1-hydroxy-1-trifluoromethyl-2,2,2-trifluoroethyl).4,4'-oxydianiline (yield: 72%; purity: 94.5%).

[Properties of 3,3'-bis(1-hydroxy-1-trifluoromethyl-2,2,2-trifluoroethyl)-4,4'-oxydianiline]

Pale purple-color powder. Melting point: 143.5-144.0° C. $^1$H-NMR (standard substance: TMS; solvent: $CD_3CN$) σ (ppm): 7.02 (dd, 2H, J=2.7, 8.0Hz), 7.03 (s, 2H), 7.11 (dd, 2H, J=1.2, 8.0Hz). $^9$F-NMR (standard substance: $CCl_3F$; solvent: $CD_3CN$) σ (ppm): -74.7 (s, 12F).

Example 4

Production of 3-(1-hydroxy-1-trifluoromethyl-2,2,2-trifluoroethyl)-4,4'-oxydianiline (Formula [5])

A 100 ml, glass, sealed container (autoclave) was charged with 5.00 g (25.0 mmol) of 4,4'-oxydianiline, 133 mg (0.999 mmol, 4 mol %) of aluminum chloride, and 15 ml of xylene, and the inside of the system was turned into a nitrogen atmosphere. Then, the temperature increase was started. After the inside temperature of the reaction liquid was set to 120° C., 12.4 g (74.9 mmol, 3 equivalents) of hexafluoroacetone were introduced. The reaction was conducted at an inside temperature of 120° C. for 6 hours.

The reaction liquid was found by gas chromatography (GC) analysis to contain 43.5% of the target compound, 3-(1-hydroxy-1-trifluoromethyl-2,2,2-trifluoroethyl)-4,4'-oxydianiline, 2.9% of 3,3'-bis(1-hydroxy-1-trifluoromethyl-2,2,2-trifluoroethyl)-4,4'-oxydianiline, and 46.6% of the total of various imines produced by the reaction of hexafluoroacetone with the amine moiety of 4,4'-oxydianiline.

Example 5

Production of 3-(1-hydroxy-1-trifluoromethyl-2,2,2-trifluoroethyl)-4,4'-oxydianiline (formula [5])

A 100 ml, glass, sealed container (autoclave) was charged with 30.0 g (150 mmol) of 4,4'-oxydianiline, 5.70 g (3.00 mmol, 20 mol %) of p-toluenesulfonic acid monohydrate, and 66.0 g (300 mmol, 2 equivalents) of hexafluoroacetone trihydrate, and the inside of the system was turned into a nitrogen atmosphere. Then, the temperature increase was started, and the inside temperature of the reaction liquid was set to 110° C. After stirring for 22 hours, the reaction liquid was cooled down.

The reaction liquid was found by gas chromatography (GC) analysis to contain 56.2% of the target compound, 3-(1-hydroxy-1-trifluoromethyl-2,2,2-trifluoroethyl)-4,4'-oxydianiline, 22.4% of 3,3'-bis(1-hydroxy-1-trifluoromethyl-2,2,2-trifluoroethyl)-4,4'-oxydianiline, 9.1% of an imine produced by the reaction of hexafluoroacetone with the amine moiety of 4,4'-oxydianiline, and 12.2% of 4,4'-oxydianiline. 50 ml of toluene and 50 ml of water were added to the reaction liquid.

After cooling, the precipitated solid matter was filtered, followed by vacuum drying. 56.5 g of crude 3-(1-hydroxy-1-trifluoromethyl-2,2,2-trifluoroethyl)-4,4'-oxydianiline (purity: 57.4%) were obtained. This crude product was recrystallized in toluene, thereby obtaining 23.2 g of the target 3-(1-hydroxy-1-trifluoromethyl-2,2,2-trifluoroethyl)-4,4'-oxydianiline (yield: 42%; purity: 71.0%).

[Properties of 3-(1-hydroxy-1-trifluoromethyl-2,2,2-trifluoroethyl)-4,4'-oxydianiline]

Pale purple-color powder. Melting point: 129.0-129.5° C. $^1$H-NMR (standard substance: TMS; solvent: $CD_3CN$ σ (ppm): 6.65 (m, 2H), 6.79 (m,2H), 6.93 (dd, 1H, J=2.9, 8.8 Hz), 7.04 (m, 1H), 7.09 (d, 1H, J=8.8 Hz). $^{19}$F-NMR (standard substance: $CCl_3F$; solvent: $CD_3CN$) σ (ppm): −74.8 (s, 6F).

Example 6

By using 3,3'-bis(1-hydroxy-1-trifluoromethyl-2,2,2-trifluoroethyl)-4,4'-oxydianiline synthesized in Example 3, there was conducted a polymerization reaction with the following compound (a) of dicarboxylic acid chloride.

[Chem. 14]

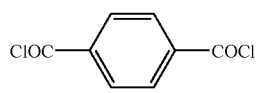

COMPOUND (a)

In the polymerization, a 100 ml, sufficiently dried, sealed, three-necked, glass flask equipped with a stirrer was charged with 40 g of dimethylacetamide, 10 g of pyridine, and 0.01 moles (5.32 g) of 3,3'-bis(1-hydroxy-1-trifluoromethyl-2,2,2-trifluoroethyl)-4,4'-oxydianiline, followed by stirring while blowing nitrogen to obtain homogenization, charging with 0.01 moles (2.02 g) of the compound (a), terephthalic acid chloride, and conducting the polymerization with stirring for 5 hours. Then, it was reprecipitated in a large amount of methanol for isolation. The isolated polymer (A) was dissolved in γ-butyrolactone, thereby obtaining a γ-butyrolactone solution of the polymer (A) (Weight average molecular weight (Mw) of the polymer (A): 9600).

[Chem. 15]

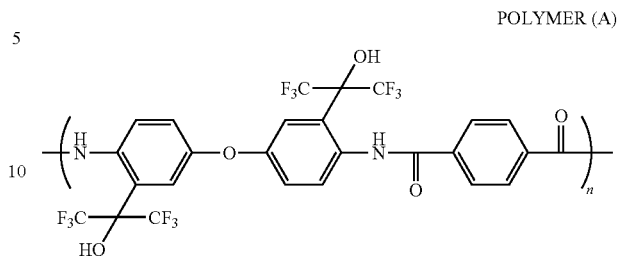

POLYMER (A)

Example 7

By using the compound (b) and the compound (c) as dicarboxylic acid dichlorides in place of the compound (a) of Example 6, respective polymerizations were conducted with 3,3'-bis(1-hydroxy-1-trifluoromethyl-2,2,2-trifluoroethyl)-4,4'-oxydianiline under similar conditions.

[Chem. 16]

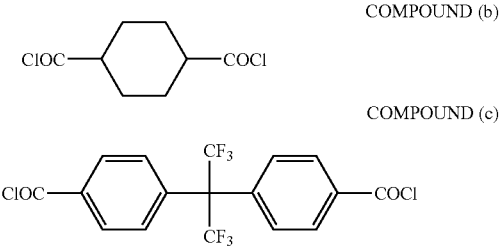

COMPOUND (b)

COMPOUND (c)

After isolation by conducting a post-treatment similar to that of Example 6, they were dissolved in γ-butyrolactone, thereby obtaining respective γ-butyrolactone solutions of polymers (B) and (C) (Weight average molecular weight of polymer (B): 10200; and Weight average molecular weight of polymer (C): 10000).

[Chem. 17]

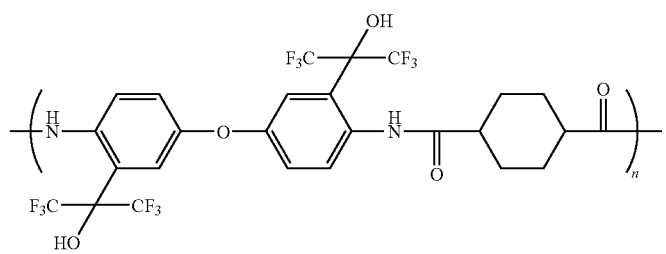

POLYMER (B)

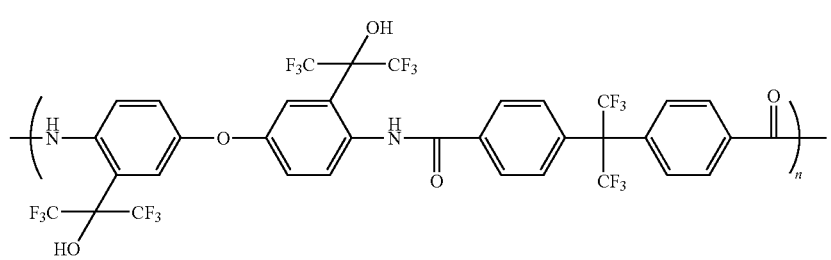

POLYMER (C)

Example 8

γ-butyrolactone solutions of polymers (A), (B) and (C) synthesized in Example 6 and Example 7 were applied to glass substrates, followed by drying at 120° C. for 2 hours, thereby obtaining transparent films in respective cases.

Then, the obtained film (thickness: 40 μm) of polymer (A) was subjected to a heating treatment at 280° C. for 2 hours, thereby obtaining a film through ring closure into polymer (D). In the measurement of thermal decomposition temperature of the obtained film, it was stably maintained even at 400° C. Dielectric constant at 1 kHz was a low value of 2.2.

[Chem. 18]

POLYMER (D)

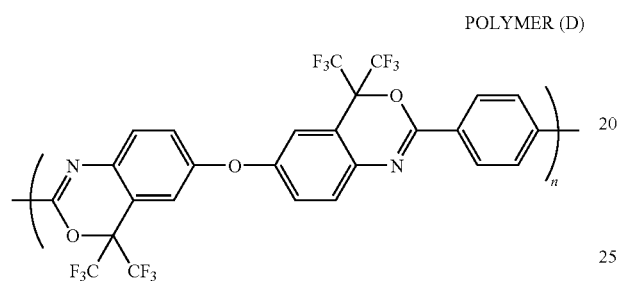

Example 9

By using 3,3'-bis(1-hydroxy-1-trifluoromethyl-2,2,2-trifluoroethyl)-4,4'-oxydianiline synthesized in Example 3, there were conducted polymerizations with the following tetracarboxylic acid anhydride compounds (d), (e) and (f),

[Chem. 19]

COMPOUND (d)

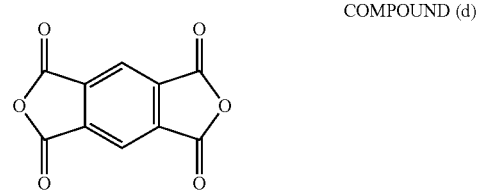

COMPOUND (e)

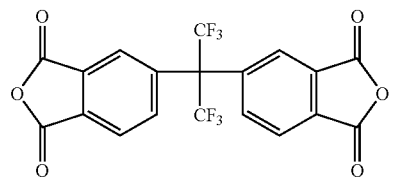

COMPOUND (f)

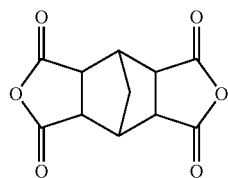

In the polymerization, a 100 ml, sufficiently dried, sealed, three-necked, glass flask equipped with a stirrer was charged with 30 g of methyl isobutyl ketone and 0.01 moles (5.32 g) of 3,3'-bis(1-hydroxy-1-trifluoromethyl-2,2,2-trifluoroethyl)-4,4'-oxydianiline, followed by stirring while blowing nitrogen to obtain homogenization, charging with 0.01 moles of the three anhydrides, the compounds (d), (e) and (f), and conducting the polymerization with stirring for 5 hours. Then, they were reprecipitated in a large amount of methanol for isolation. The isolated polymers (E), (F) and (G) were each dissolved in γ-butyrolactone, thereby obtaining three of polymer solutions (Weight average molecular weight (Mw) of the polymer (E): 10500; Weight average molecular weight (Mw) of the polymer (F): 9900; and Weight average molecular weight (Mw) of the polymer (G): 10000).

These polymer solutions were applied to silicon wafers, thereby producing homogeneous, transparent films.

[Chem. 20]

POLYMER (E)

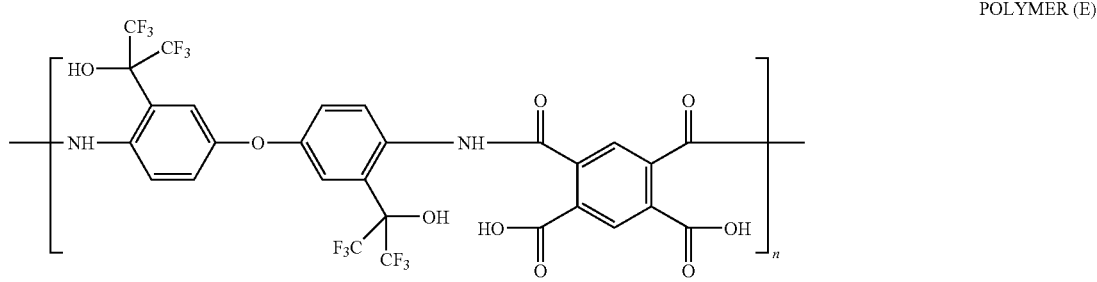

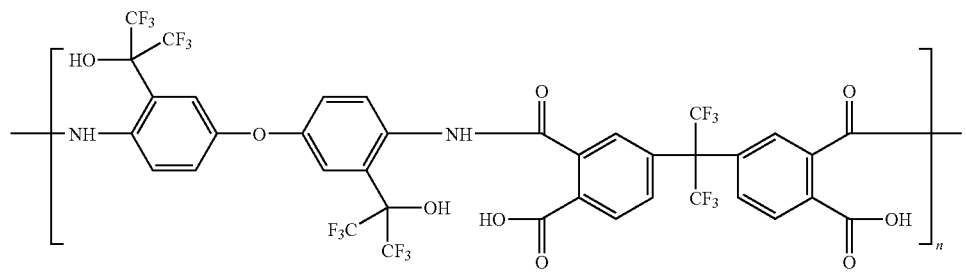

POLYMER (F)

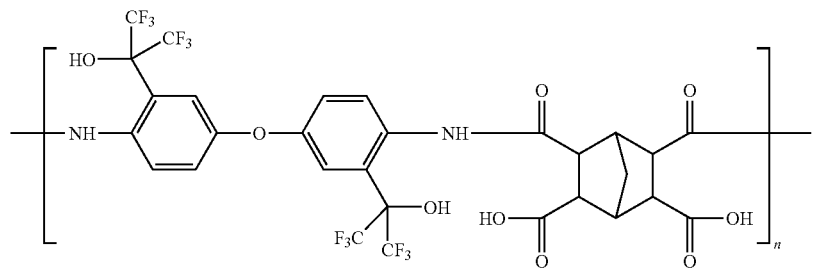

POLYMER (G)

Example 10

γ-butyrolactone solutions were prepared in a manner that the polymers (E), (F) and (G) obtained in Example 9 become 10% in solid content, followed by addition of acetic anhydride and pyridine and stirring at 50° C. for 2 hr for mixing, thereby conducting imidizations by chemical reactions. The obtained polymer solutions were reprecipitated in methanol, followed by three-times repetitive washing with stirring with clean methanol and then drying at room temperature. Although imide cyclizations were confirmed in the obtained polymer solids, they were found to be soluble in dimethylacetamide and to be soluble polyimides (H), (I) and (J). Then, dimethylacetamide solutions were respectively prepared in a manner that (H), (I) and (J) become 12% in solid content, followed by spin coatings on silicon wafers, thereby obtaining fluorine-containing polymer films. On the other hand, the films of the polymer (E), (F) and (G) were subjected to a heat treatment at 350° C. for 1 hour. With this, similar dehydration reactions occurred, thereby producing the polyimides (H), (I) and (J).

Then, the thermal decomposition temperatures of the polymers (H), (I) and (J) were measured by DSC (differential scanning calorimeter).With this, they showed high heat resistances of 450° C., 445° C. and 430° C. in terms of 5% weight reduction temperature. Furthermore, their dielectric constants at 1 MHz were measured by using an LCR meter. With this, they respectively showed low values of 2.9, 2.7 and 2.6.

[Chem. 21]

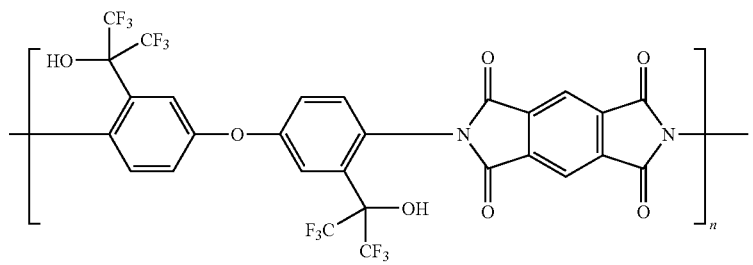

POLYMER (H)

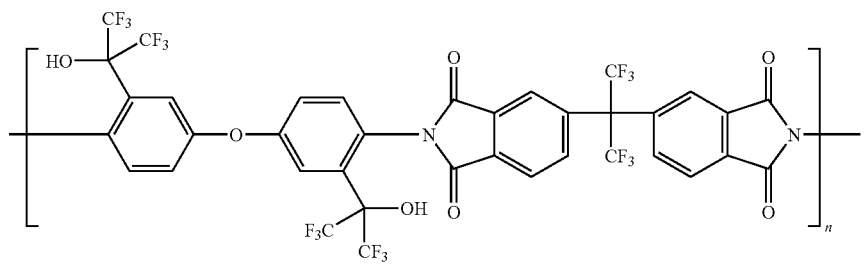

POLYMER (I)

POLYMER (J)

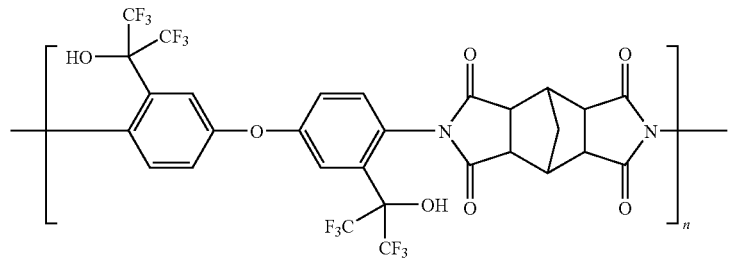

What is claimed is:
1. A fluorine-containing polymerizable monomer represented by the formula [1],

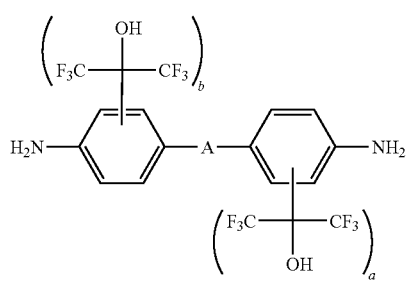

[1]

wherein A represents a single bond, oxygen atom, sulfur atom, CO, CH$_2$, SO, SO$_2$, C(CH$_3$)$_2$, NHCO, C(CF$_3$)$_2$, phenyl, or aliphatic ring; each of "a" and "b" independently represents an integer of 0-2; and $1 \leqq a+b \leqq 4$.

2. A fluorine-containing polymerizable monomer represented by the formula [2],

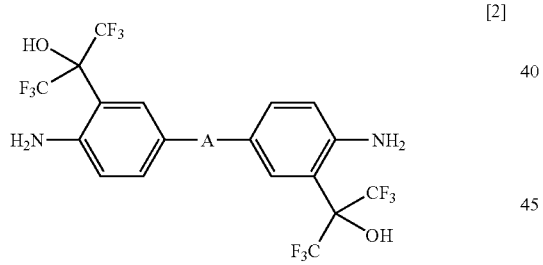

[2]

wherein A represents a single bond, oxygen atom, sulfur atom, CO, CH$_2$, SO, SO$_2$, C(CH$_3$)$_2$, NHCO, C(CF$_3$)$_2$, phenyl, or aliphatic ring.

3. A fluorine-containing polymerizable monomer represented by the formula [3],

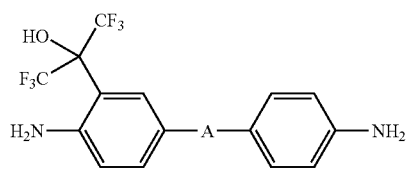

[3]

wherein A represents a single bond, oxygen atom, sulfur atom, CO, CH$_2$, SO, SO$_2$, C(CH$_3$)$_2$, NHCO, C(CF$_3$)$_2$, phenyl, or aliphatic ring.

4. 3,3'-bis(1-hydroxy-1-trifluoromethyl-2,2,2-trifluoroethyl)-4,4'-oxydianiline represented by the formula [4]

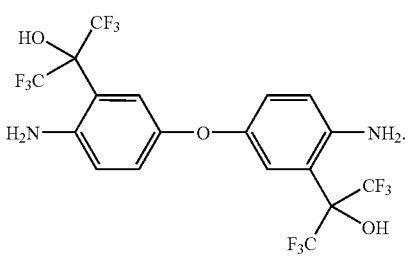

[4]

5. 3-(1-hydroxy-1-trifluoromethyl-2,2,2-trifluoroethyl)-4,4'-oxydianiline represented by the formula [5]

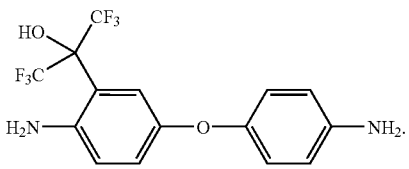

[5]

6. A fluorine-containing polymerizable monomer according to claim 1, wherein A of the formula [1] represents CH$_2$.
7. a fluorine-containing polymerizable monomer according to claim 2, wherein A of the formula [2] represents CH$_2$.

* * * * *

UNITED STATES PATENT AND TRADEMARK OFFICE
CERTIFICATE OF CORRECTION

PATENT NO. : 7,629,434 B2
APPLICATION NO. : 10/586184
DATED : December 8, 2009
INVENTOR(S) : Saegusa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 663 days.

Signed and Sealed this

Twenty-first Day of December, 2010

David J. Kappos
*Director of the United States Patent and Trademark Office*